United States Patent [19]

Takahashi

[11] Patent Number: 5,057,080
[45] Date of Patent: Oct. 15, 1991

[54] MEDICAL SUCTION TUBE AND SUCTION CONTROL APPARATUS FOR ENDOSCOPE

[75] Inventor: Nagashige Takahashi, Tokyo, Japan

[73] Assignee: Asahi Kogaku Kogyo Kabushiki Kaisha, Tokyo, Japan

[21] Appl. No.: 330,465

[22] Filed: Mar. 30, 1989

[30] Foreign Application Priority Data

| Apr. 8, 1988 | [JP] | Japan | 63-47919[U] |
| Apr. 13, 1988 | [JP] | Japan | 63-50129[U] |
| Dec. 20, 1988 | [JP] | Japan | 63-321099 |

[51] Int. Cl.⁵ ............................................. A61M 25/00
[52] U.S. Cl. ................................. 604/118; 604/129; 604/247; 251/342
[58] Field of Search ............... 604/118, 119, 128, 129, 604/247; 128/4–6; 251/4, 342

[56] References Cited

U.S. PATENT DOCUMENTS

| 1,574,149 | 2/1926 | Hompes et al. | 137/147 |
| 2,690,734 | 10/1954 | Heckendorf | 251/342 |
| 4,412,531 | 11/1983 | Chikashige | |
| 4,485,812 | 12/1984 | Harada et al. | |
| 4,737,152 | 4/1988 | Alchas | 604/247 |

FOREIGN PATENT DOCUMENTS

| 0007602 | 2/1980 | European Pat. Off. | |
| 1566626 | 7/1967 | Fed. Rep. of Germany | |
| 2950323 | 4/1981 | Fed. Rep. of Germany | |
| 8302900 | 9/1983 | World Int. Prop. O. | |

Primary Examiner—Stephen C. Pellegrino
Assistant Examiner—Ralph A. Lewis
Attorney, Agent, or Firm—Sandler, Greenblum, & Bernstein

[57] ABSTRACT

A medical suction tube which is opened at the distal end thereof and connected at the proximal end thereof to a suction means. A linear cut is made in the intermediate portion of the tube so as to extend obliquely from the proximal end side toward the distal end side of the tube so that, when the tube is bent, the cut is opened and ambient air is sucked into the tube through the cut, whereas, when the tube is straightened, the cut is closed and suction is performed through the distal end opening. A suction control apparatus for an endoscope that utilizes the above-described medical suction tube. The suction control apparatus has a switching element for switching over the following two states from one to the, that is, a state wherein the tube is bent with the cut facing outward and a state wherein the tube is straightened at and near the cut, so that, when the tube is bent, the cut is opened and the ambient air is sucked into the tube through the cut, whereas, when the tube is straightened, the cut is closed and suction is performed through a suction port at the distal end of the endoscope.

19 Claims, 6 Drawing Sheets

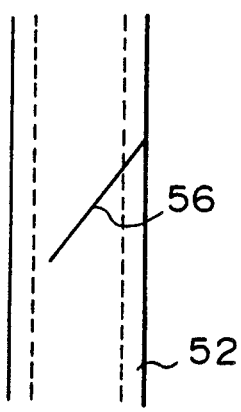
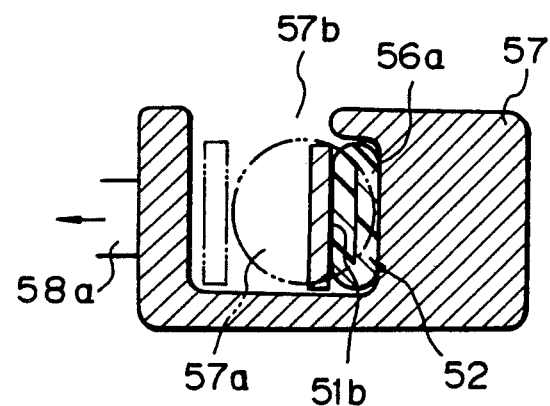
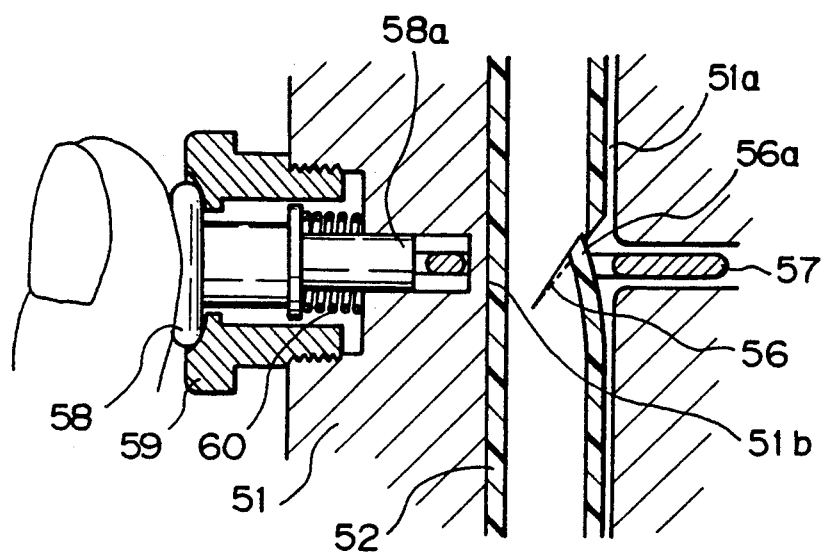

MEDICAL SUCTION TUBE AND SUCTION CONTROL APPARATUS FOR ENDOSCOPE

BACKGROUND OF THE INVENTION

1. Field of the Invention

The present invention relates to a medical suction tube employed to suck mucus and mucous membrane from a hollow organ of the patient's body and also pertains to a suction control apparatus for an endoscope that utilizes such a suction tube.

2. Description of the Related Art

A typical conventional medical suction tube has an on-off valve connected to the intermediate portion of the tube so that the tube is opened and closed by the valve. However, in the case where the tube is made disposable for sanitary reasons, for example, the valve which comes into contact with the sucked mucus and mucous membrane must also be disposed of after use for a single procedure and, therefore, the cost becomes considerably high.

To overcome the above-described disadvantage, there has heretofore been a prior art wherein a flexible tube is closed by pressing it sideward and, when the tube is released from the pressure, the tube returns to its previous open state by its own restoring force. With this prior art device, the sucked mucus and mucous membrane do not come into contact with any other elements than the tube and, therefore, it is only necessary to dispose of the tube alone after use for a single procedure.

However, this prior art medical suction tube necessitates an operation of closing the tube itself by pressing it sideward and this operation requires the application of a great deal of force continuously for a certain period of time.

It may be considered is possible to reduce the wall thickness of the tube in order to minimize the amount of force required to press the tube. However, a reduction in the wall thickness of the tube lowers the restoring force of the tube which is expected to act when the tube is released from the pressure, or may cause the tube to be closed when the suction force is applied thereto and results in a failure to effect a suction operation.

A suction control apparatus for an endoscope is usually provided on the control part of the endoscope and, in many cases, the suction control apparatus has a structure wherein a piston is reciprocatably fitted in a cylinder connected to a suction tube which opens at the distal end of the insert part of the endoscope.

In such a suction control apparatus, however, the number of parts is large and the structure is complicated and, therefore, the parts are likely to be clogged with the mucus and mucous membrane sucked through the tube. The mucus and mucous membrane are considerably difficult to wash off completely and therefore give rise to unsanitary conditions.

Under these circumstances, there has heretofore been a suction control apparatus wherein the suction tube is normally closed by pressing it sideward within the control part and, when a suction operation is to be conducted, the suction tube is opened by removing the pressure therefrom. With this arrangement, the sucked mucus and mucous membrane do not come into contact with any other elements than the tube and, therefore, washing conducted after use is facilitated. However, a great deal of force is needed to press the tube itself sidewardly so as to close it, and the operability of the prior art is therefore considerably low.

The amount of force required to press the tube may be minimized by reducing the wall thickness of the tube. However, a reduction in the wall thickness of the tube lowers the restoring force of the tube which is expected to act when the tube is released from the pressure, or may cause the tube to be closed when the suction force is applied thereto and result in a failure to effect a suction operation, as in the case of the above-described medical suction tube.

SUMMARY OF THE INVENTION

An object of the present invention is to provide a medical suction tube which is designed so that a suction operation can be effectively and reliably controlled with an extremely simple structure and with a small amount of force, and also provide a suction control apparatus for an endoscope which facilitates washing and is highly sanitary and which further has a simple structure and enables a suction operation to be controlled with a small amount of force.

Other objects and advantages of the present invention will become apparent from the following detailed description of illustrated embodiments of the invention.

According to the present invention, there is provided a medical suction tube connected at the proximal end thereof to a suction means, comprising: an opening formed at the distal end of the tube; and a cut made in the intermediate portion of the tube so as to extend obliquely from the proximal end side toward the distal end side of the tube, whereby, when the tube is bent, the cut is opened and ambient air is sucked into the tube through the cut, and, when the tube is straightened, the cut is closed and suction is performed through the opening.

In addition, there is provided a suction control apparatus provided on a control part of an endoscope having a suction port at the distal end of an insert part thereof, comprising: a flexible tube communicating at the distal end thereof with the suction port and communicably connected at the proximal end thereof to a suction means; a cut made in the intermediate portion of the tube so as to extend obliquely from the proximal end side toward the distal end side of the tube; and a switching device for switching over the following two states from one to the other; that is, a state wherein the tube is bent with the cut facing outward and a state wherein the tube is straightened at and near the cut, whereby, when the tube is bent, the cut is opened and ambient air is sucked into the tube through the cut, whereas, when the tube is straightened, the cut is closed and suction is performed through the suction port.

In addition, there is provided a suction control apparatus provided on a control part of an endoscope having a suction port at the distal end of an insert part thereof, comprising: a flexible tube communicating at the distal end thereof with the suction port and communicably connected at the proximal end thereof to a suction means; a cut made in the intermediate portion of the tube so as to extend obliquely from the proximal end side toward the distal end side of the tube; and a switching device for switching over the following two states from one to the other; that is, a stand-by state wherein the tube is diametrically pressed at the cut from the side of the tube where the cut is provided so as to close the cut area which leads to the distal end of the tube and a suction state wherein the tube is restored to its free state, thereby enabling suction to take place from the distal end side to the proximal end side of the tube.

BRIEF DESCRIPTION OF THE DRAWINGS

The present invention may be more fully understood from the description of preferred embodiments of the invention set forth below, together with the accompanying drawings, in which:

FIG. 9 is a fragmentary sectional side view of the suction control apparatus in a state wherein the control button is pushed in;

FIG. 12 is a fragmentary side view of a tube employed in the suction control apparatus shown in FIG. 11;

FIG. 13 is a sectional plan view of the pressing plate and the tube employed in the suction control apparatus shown in FIG. 11; and FIG. 14 is a fragmentary enlarged sectional side view of the suction control apparatus shown in FIG. 11 in a state wherein the control button is pushed in.

DESCRIPTION OF THE EMBODIMENTS

Embodiments of the present invention will be described below in detail with reference to the accompanying drawings.

Figure 1:
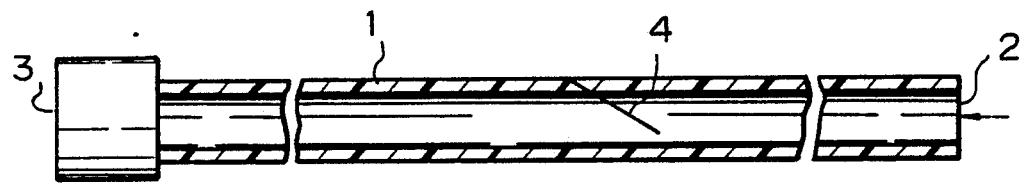
FIG. 1 is a sectional side view of a first embodiment of the medical suction tube according to the present invention.
Figure 2:
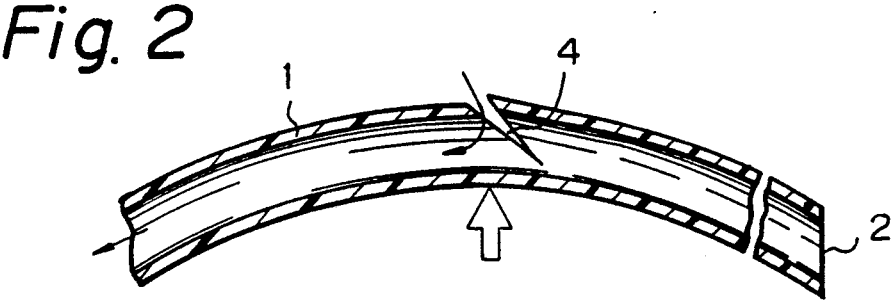
FIG. 2 is a sectional side view of the tube shown in FIG. 1, which shows the tube in a bent state.

FIGS. 1 and 2 show in combination a first embodiment of the medical suction tube according to the present invention. In the figures, the reference numeral 1 denotes a flexible tube which is made, for example, of elastomer, tetrafluoroethylene resin, etc. Therefore, the tube 1 has superior chemical resistance. The tube 1 has an open distal end which is defined as a distal end opening 2. The proximal end of the tube 1 is connected to a suction means 3. It should be noted that the opening 2 may be provided on the side of the tube 1.

A linear cut 4 is made in the intermediate portion of the tube 1 so as to extend obliquely from the proximal end side toward the distal end side of the tube 1. For example, the cut 4 is made with a sharp-edged tool such as a razor so that the cut 4 is at 30 degrees to the axis of the tube 1 and extends to a depth which is equal to about two thirds of the diameter of the tube 1.

The arrangement is such that, when the tube 1 is straightened at and near the cut 4, the cut 4 is closed as shown in FIG. 1, whereas, when the tube 1 is bent with the cut 4 facing outward, the cut 4 is opened to the open air as shown in FIG. 2.

In the first embodiment arranged as described above, the tube 1 is formed such that it is normally straight at and near the cut 4 and hence the cut 4 is closed in a normal state, as shown in FIG. 1. Accordingly, if the suction means 3 is activated in this state, suction is performed through the distal end opening 2. This embodiment is therefore suitable for uses in which suction is steadily conducted.

When the tube 1 is pushed from one side thereof so that the tube 1 is bent with the cut 4 facing outward, the cut 4 is opened to the open air, as shown in FIG. 2. Accordingly, the air is sucked into the tube 1 through the cut 4 and the suction through the distal end opening 2 is suspended.

Figure 3:
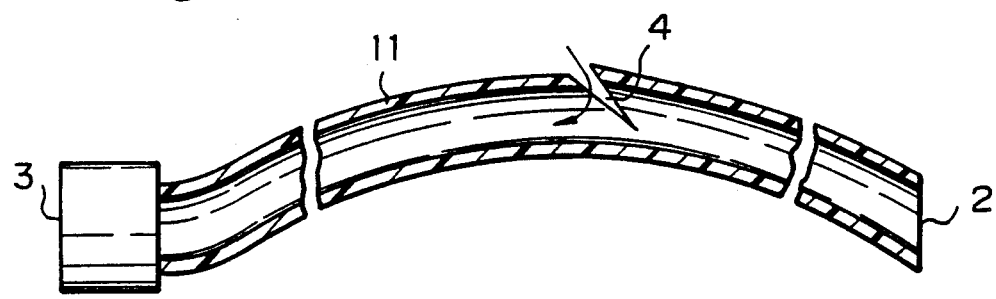
FIG. 3 is a sectional side view of a second embodiment of the medical suction tube according to the present invention.
Figure 4:
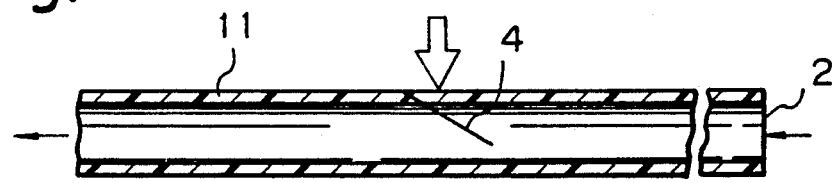
FIG. 4 is a sectional side view of the tube shown in FIG. 3, which shows the tube in a straightened state.

FIGS. 3 and 4 show in combination a second embodiment of the present invention, in which a tube 11 is bent so that the cut 4 normally opens to ambient air. Accordingly, opposite to the first embodiment, this embodiment is arranged such that, when the tube 11 is in a normal state, the air is sucked through the cut 4 and no suction is performed through the distal end opening 2, as shown in FIG. 3. When the tube 11 is straightened, the cut 4 is closed and suction is performed through the distal end opening 2, as shown in FIG. 4.

The effects of the direction and depth of the cut 4 in each embodiment have been confirmed by the following experiments.

Figure 5:
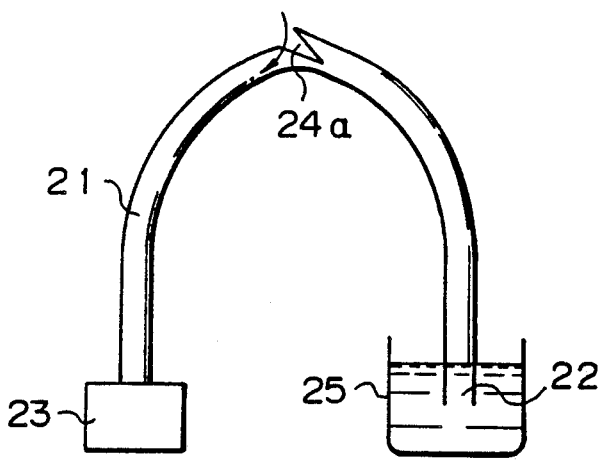
FIGS. 5 to 7 are sectional side views, respectively, showing first to third experiments.
Figure 6:
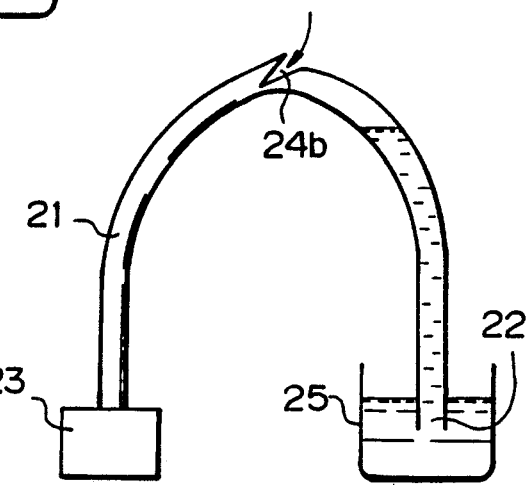
Figure 7:
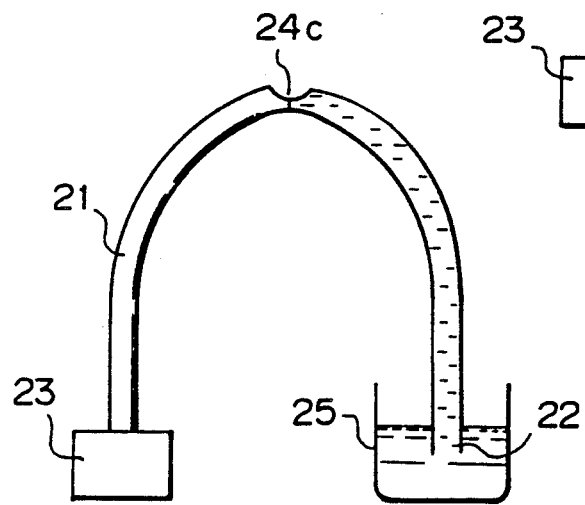

FIGS. 5 to 7 show first to third experiments, respectively, which were conducted under the same conditions except for the cuts 24a, 24b and 24c made in the respective tubes 21. In these experiments, flexible tubes 21 having an inner diameter of 2.6 mm and an outer diameter of 4 mm were used and water contained in a water tank was sucked through the distal end opening 22 by a suction means 23 (the vacuum used being about 250 mmHg) connected to the proximal end of each of the tubes 21. Each tube 21 was bent in the form of an arc having a radius of about 25 mm. In the experiments, the cuts 24a, 24b and 24c were disposed at the respective tops of the bent tubes 21 so as to normally open to ambient air.

In the first experiment, the cut 24a was, as shown in FIG. 5, linearly made in the tube 21 so as to extend obliquely from the proximal end side (i.e., the suction means side) toward the distal end side (i.e., the distal end opening side) of the tube 21 in the same way as in the above-described embodiments. In this experiment, a large amount of air was sucked into the tube 21 through the cut 24a and, therefore, substantially no water was sucked up into the distal end opening 22, as shown in FIG. 5.

In the second experiment, the cut 24b was, as shown in FIG. 6, made in the tube 21 so as to extend obliquely from the distal end side toward the proximal end side of the tube 21 in reverse relation to the first experiment. In this case also, the air was sucked into the tube 21 through the cut 24b. However, in contrast to the first experiment, a vacuum was produced in the tube 21 between the cut 24b and the distal end opening 22 and water was sucked up into the tube 21 as far as the vicinity of the cut 24b.

In the third experiment, the cut 24c was formed by boring a hole in the tube 21 from one side thereof, the hole having a diameter of about 4 mm in the axial direction of the tube 21. In this case, a high vacuum was produced in the tube 21 between the cut 24c and the distal end opening 22 and water was sucked up as far as the cut 24c. As a result, a small amount of water leaked out through the cut 24c and also a small amount of water was sucked into the suction means 23.

It will be clear from the above-described experimental results that, if a cut is linearly made in the tube 21 so as to extend obliquely from the proximal end side toward the distal end side of the tube 21 as in the case of the cut 24a, when the tube 21 was bent with the cut facing outward, substantially no vacuum acts at the distal end opening 22 of the tube 21.

Although in the above-described embodiments the angle of the cut 4 to the axis of the tube 1 is set at 30 degrees and the depth of the cut 4 is set at about two thirds of the diameter of the tube 1, it should be noted that the present invention is not necessarily limited thereto. More specifically, the angle and depth of the cut may be set as desired, provided that a cut is linearly made in the tube such as to extend obliquely from the proximal end side toward the distal end side of the tube so that, when the tube is straightened at and near the cut, the cut is closed, whereas, when the tube is bent with the cut facing outward, the cut is opened to ambient air and substantially no suction is performed through the distal end opening. In practical use, the angle of the cut to the axis of the tube is preferably set in the range of from 15 to 60 degrees.

Thus, according to the medical suction tube of the present invention, a flexible tube itself is provided with a cut so that the suction operation is controlled by bending or straightening the tube. Accordingly, the structure of the suction tube is extremely simple and the cost thereof is considerably low; therefore, it is possible to make it disposable. In addition, it is possible to control a suction operation with ease. Since the operability is not impaired even if a hard plastic tube is employed, it is possible to select a tube having a necessary level of hardness so as to conduct an effective and reliable suction operation.

Figure 8:
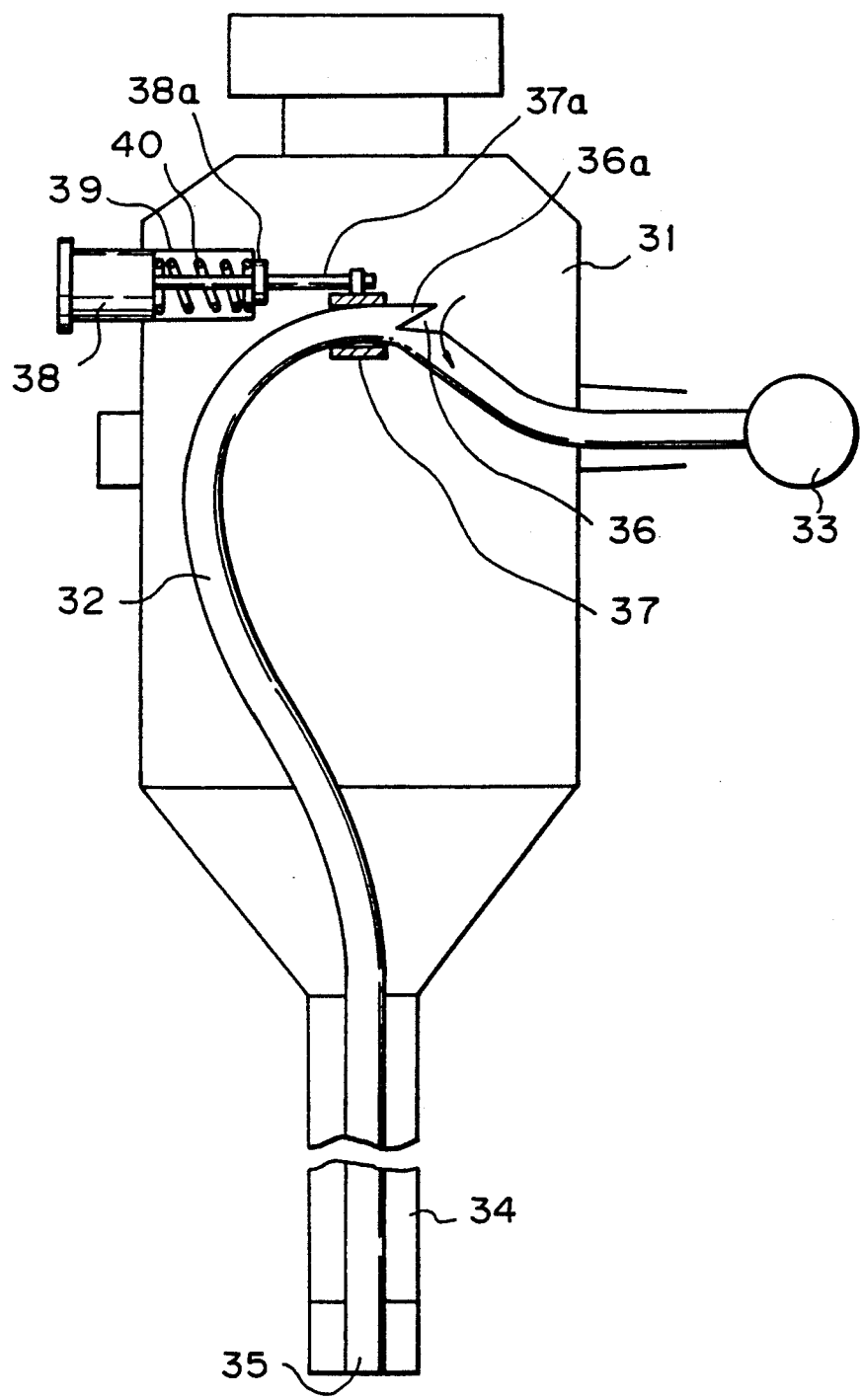
FIG. 8 is a schematic view showing the general arrangement of an endoscope incorporating one embodiment of the suction control apparatus according to the present invention.

FIG. 8 shows an embodiment in which the above-described medical suction tube is applied to a suction control apparatus for an endoscope.

In FIG. 8, the reference numeral 31 denotes a control part of an endoscope. A flexible tube 32 made, for example, of elastomer, tetrafluoroethylene, etc., is disposed inside the control part 31. The proximal end of the tube 32 is communicably connected with a suction means 33, while the distal end of the tube 32 is communicably connected with a suction port 35 which is opened at the distal end of the insert part 34 of the endoscope. Accordingly, it is possible to suck up mucus and mucous membrane from a hollow organ of the patient's body into the suction means 33 from the suction port 35 through the tube 32. It should be noted that the tube 32 may be disposed along the outside of the control part 31 and the insert part 34 and may also be arranged so as to be detachable from to the endoscope.

Figure 9:
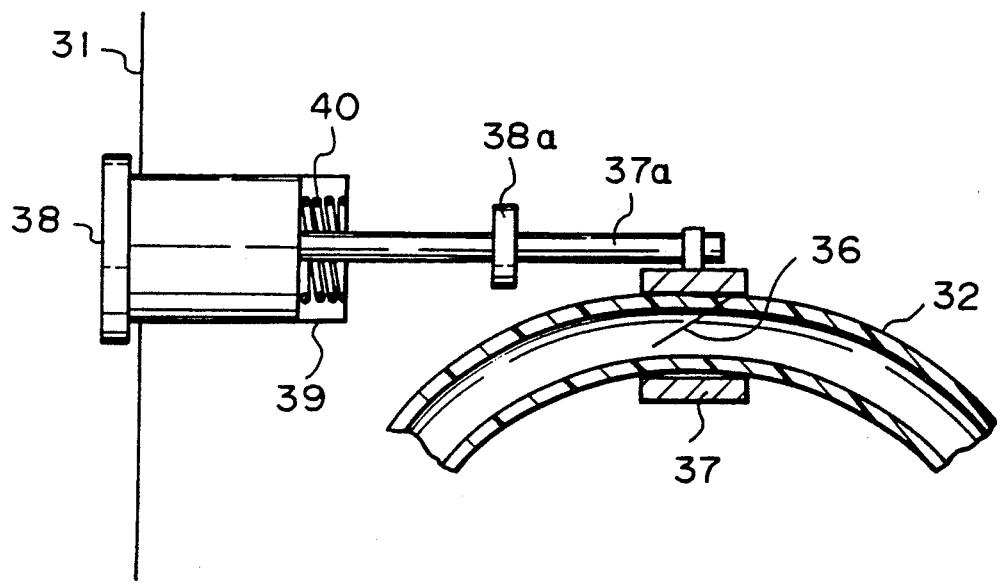

The tube 32 is disposed in such a manner that it is bent inside the control part 31. A linear cut 36 is made in the outer side of the bent portion of the tube 32 so as to extend obliquely from the proximal end side toward the distal end side of the tube 32. For example, the cut 36 is made with a sharp-edged toll such as a razor so that the cut 36 is at 30 degrees to the axis of the tube 32 and extends to a depth which is equal to about two thirds of the diameter of the tube 32. In practical use, the angle of the cut 36 should be selected so as to fall within the range of from 15 to 60 degrees. The arrangement is such that, when the tube 32 is bent with the cut 36 facing outward, the cut 36 is opened to the ambient air as shown in FIG. 8, whereas, when the tube 32 is straightened at and near the cut 36, the cut 36 is closed as shown in FIG. 9.

The control part 31 is provided with a slider 37 which is slidable along the outer surface of the tube 32. The slider 37 is formed in a tubular shape so that, when the tube 32 is curved, that portion of the tube 32 which is within the slider 37 extends substantially straight. Accordingly, when that portion of the tube 32 which is provided with the cut 36 is within the slider 37, a flap 36a which is formed at the distal end side of the cut 36 is pressed by the slider 37 so as to close the cut 36, thereby preventing ambient air from entering the tube 32 through the cut 36.

The slider 37 is coupled to a control button 38 through a connecting rod 37a. The control button 38 is reciprocatably fitted in a cylinder 39 which is secured to the control part 31. The control button 38 is constantly biased outward (leftward as viewed in FIG. 8) by the action of a compression coil spring 40 which is interposed between the control button 38 and the cylinder 39. Accordingly, in a stand-by state, the slider 37 is at a position which is closer to the suction port 35 than the cut 36. When the control button 38 is pushed in, the slider 37 slides along the outer surface of the tube 32 to a position where it covers the cut 36. The reference numeral 38a denotes a stopper for the control button 38.

The operation of the embodiment arranged as described above will be explained below.

In a stand-by state, the cut 36 opens to the open air, as shown in FIG. 8. Accordingly, when the suction means 33 is activated in this state, the air is sucked into the tube 32 through the cut 36 and no suction is performed through the suction port 35.

When the control button 38 is pushed in as shown in FIG. 9, the slider 37 presses the flap 36a so as to close the cut 36, thereby preventing the air from entering the tube 32 through the cut 36, and thus enabling suction to take place through the suction port 35 at the distal end of the insert part 34. At this time, the cut 36 is completely covered with the slider 37 and thereby entirely shielded from air and it is therefore possible to eliminate completely the fear that the sucked mucus and mucous membrane will leak out through the cut 36.

Figure 10:
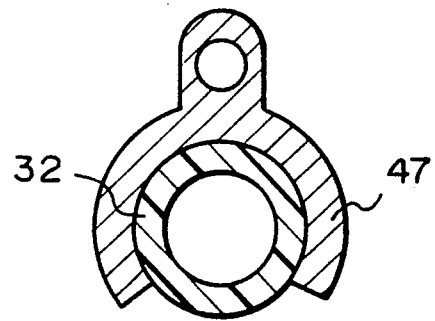
FIG. 10 is a sectional front view of a slider having a C-shaped cross-sectional configuration.

It should be noted that the slider 37 may be formed in a C-shaped cross-sectional configuration as shown by the reference numeral 47 in FIG. 10. By doing so, the tube 32 can be readily attached to and removed from the slider 47 through the opening in the C-shaped configuration.

Thus, according to the endoscope suction control apparatus of the present invention, the sucked mucus and mucous membrane come into contact only with the inner surface of the tube and it is therefore possible to conduct washing readily and completely after use of the endoscope. Accordingly, the suction control apparatus of the present invention is highly sanitary.

Since a suction operation can be controlled simply by bending or straightening a tube provided with a cut, the structure of the suction control apparatus is simple and it is possible to operate the apparatus with a relatively small amount of force. In addition, since the tube has a simple structure and is less costly, it is enable to be disposed of after use for a single procedure.

Figure 11:
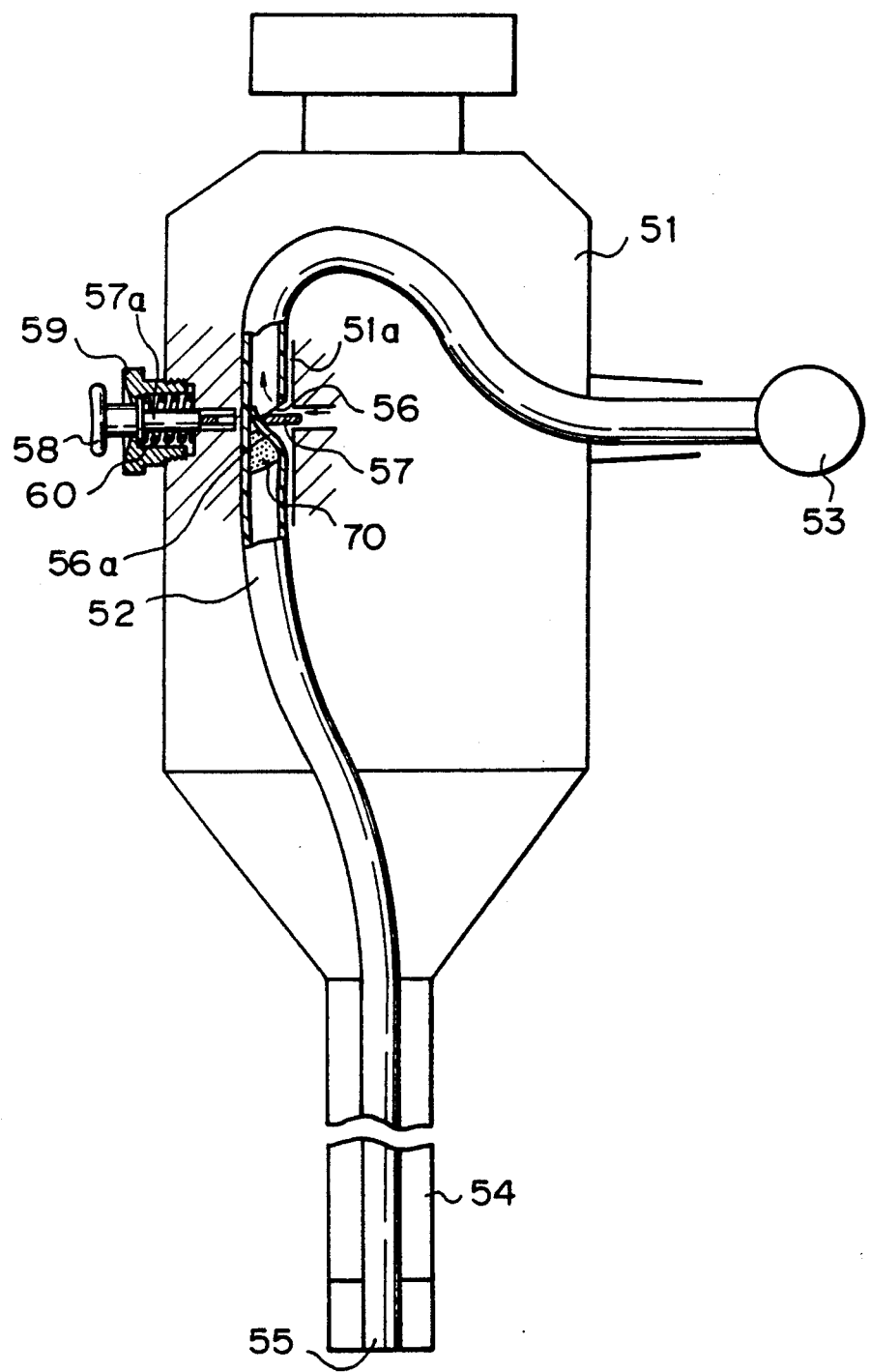
FIG. 11 is a schematic view showing the general arrangement of an endoscope incorporating another embodiment of the suction control apparatus according to the present invention.

FIG. 11 shows another embodiment of the suction control apparatus for an endoscope according to the present invention. In this figure, the reference numeral 51 denotes a control part of an endoscope. A flexible tube 52 made, for example, of elastomer, tetrafluoroethylene, etc., is disposed inside the control part 51. The proximal end of the tube 52 is communicably connected with a suction means 53, while the distal end of the tube 52 is communicably connected with a suction port 55 which is opened at the distal end of the insert part 54 of the endoscope. Accordingly, it is possible to suck up mucus and mucous membrane from a hollow organ of the patient's body into the suction means 53 from the suction port 55 through the tube 52.

It should be noted that the tube 52 may be disposed along the outside of the control part 51 and the insert part 54 and may also be arranged so as to be detachable from the endoscope. The intermediate portion of the tube 52 may be constructed of a plurality of tube members which are connected in series.

That portion of the tube 52 which is within the control part 51 is provided with a linear cut 56 which extends obliquely from the proximal end side (i.e., the suction means side) toward the distal end side of the tube 52, as also shown in FIG. 12. For example, the cut 56 is made with a sharp-edged tool such as a razor so that the cut 56 is at 30 degrees (any angle within the range of from 15 to 60 degrees being possible to select) to the axis of the tube 52 and extends to a depth which is equal to about two thirds of the diameter of the tube 52. A flap 56a which is formed at the distal end of the cut 56 is set in such a manner that the outer surface of the tip of the flap 56a is disposed at the inner side of that portion of the tube 52 which is at the proximal end side of the cut 56, as shown in FIG. 14.

Referring back to FIG. 11, the control part 51 is provided with a pressing plate 57 which is slidable in the diametrical direction of the tube 52 so that the pressing plate 57 can press the flap 56a from the side of the tube 52 where the cut 56 is provided so as to close the tube 52. As shown in FIG. 13, the pressing plate 57 is provided with a bore 57a for receiving the tube 52. The wall of the bore 57a which is pressed against the tube 52 is formed so as to extend in a straight line. One side of the bore 57a is open as shown by the reference numeral 57b so that the tube 57a can be inserted into and removed from the bore 52 therethrough when the tube 52 is assembled or replaced.

That portion of the tube 52 which is at and near the cut 56 is inserted into a guide groove 51a formed in the control part 51 so that said portion of the tube 52 will not be moved in the direction in which the flap 56a is pressed by the pressing plate 57. Accordingly, when the flap 56a is pressed by the pressing plate 57 from the side of the tube 52 wherein the cut 56 is provided, the flap 56a is pressed against the wall of the tube 52 which abuts on the inner wall 51b of the control part 51, thus closing the cut area which leads to the distal end portion of the tube 52, as shown in FIGS. 11 and 13.

The pressing plate 57 is coupled to a control button 58 through a connecting rod 58a. The control button 58 is reciprocatably fitted in a retaining member 59 and constantly biased outward (leftward as viewed in FIG. 11) by the action of a compression coil spring 60 which is interposed between the control button 58 and the control part 51. Accordingly, in a stand-by state, the pressing plate 57 constantly presses the tube 52. However, when the control button 58 is pushed in, the pressing plate 57 is moved away from the tube 52, thus releasing the tube 52 from the pressed state.

The operation of the embodiment arranged as described above will next be explained. In a stand-by state, the tube 52 is pressed by the pressing plate 57, as shown in FIGS. 11 and 13. Thus, since the cut area that leads to the suction port 55 at the distal end of the insert part 54 is closed, even if the suction means 53 is activated, no suction is performed through the suction port 55 but ambient air is sucked into the tube 52 through the open cut 56 instead. At this time, even if mucus and mucous membrane enter the tube 52 through the suction port 55 due to, for example, a rise in pressure inside a hollow organ of the patient's body, the mucus mucous membrane are blocked by the reverse side of the flap 56a that is closing the tube 52, as shown by the reference numeral 70 in FIG. 11. If the tube 52 should be incompletely closed at said portion, the mucus and mucous membrane 70 are sucked up in small amounts toward the suction means 53 which is activated at all times and there is no fear of the mucus and mucous membrane 70 leaking to the outside.

When the control button 58 is pushed in as shown in FIG. 14, the tube 52 is released from the pressed state and the cut 56 in the tube 52 is closed so that no air enters the tube 52 through the cut 56. In consequence, suction is performed through the suction port 55 at the distal end of the insert part 54. At this time, the flap 56a that is at the distal end side of the cut 56 is restored to its previous position by virtue of the resilience and the outer surface of the tip of the flap 56a is pressed against the inner side of that portion of the tube 52 which is at the proximal end side of the cut 56, as shown in FIG. 14. Accordingly, there is no fear of the sucked mucus and mucous membrane leaking out at this portion of the tube 52.

If the tube 52 is covered at and near the cut 56 with a non-rigid bag member, leakage prevention becomes even more effective, so that, if the sucked mucus and mucous membrane should leak out through the cut 56, it is possible to prevent them from leaking to the outside.

Thus, the endoscope suction control apparatus according to the present invention enables a suction state and a stand-by state to be switched over from one to the other simply be sidewardly pressing that portion of the tube which is provided with a cut. Therefore, the apparatus is extremely simple in structure and requires only a small amount of force to operate the apparatus and therefore is superior in operability. As a result, it is possible to employ a thick-walled tube and hence possible to completely prevent crushing of the tube during suction.

Further, in the suction control apparatus of the present invention, the sucked mucus and mucous membrane come into contact only with the inner surface of the tube and it is therefore possible to arrange the apparatus such that the tube alone is disposed of after use so as to prevent the transmission of bacteria and viruses from one patient to another. Thus, the suction control apparatus of the present invention is also highly sanitary of view.

While the invention has been described by reference to specific embodiments chosen for purposed of illustration, it should be apparent that numerous modifications could be made thereto by those skilled in the art without departing from the basic concept and scope of the invention.

What is claimed is:

1. A suction control apparatus provided on a control part of an endoscope having a suction port at the distal end of an insert part thereof, comprising:
- a flexible tube communicating at the distal end thereof with said suction port and communicably connected at the proximal end thereof to a suction means;
- a cut made in the intermediate portion of said tube so as to extend obliquely; and
- switching means to bend and straighten a portion of said tube for switching over the following two states from one to the other, that is, a state wherein said tube is bent with said cut facing outward and a state wherein said tube is straightened at and near said cut,
- whereby, when said tube is bent, said cut is opened and ambient air is sucked into said tube through said cut, whereas, when said tube is straightened, said cut is closed and suction is performed through said suction port.

2. A suction control apparatus provided on a control part of an endoscope having a suction port at the distal end of an insert part thereof, comprising:
- a flexible tube communicating at the distal end thereof with said suction port and communicably connected at the proximal end thereof to a suction means;
- a cut made in the intermediate portion of said tube so as to extend obliquely from the proximal end side toward the distal end side of said tube; and
- switching means to bend and straighten a portion of said tube for switching over the following two states from one to the other, that is, a state wherein said tube is bent with said cut facing outward and a state wherein said tube is straightened at and near said cut,
- whereby, when said tube is bent, said cut is opened and ambient air is sucked into said tube through said cut, whereas, when said tube is straightened, said cut is closed and suction is performed through said suction port.

3. A suction control apparatus according to claim 2, wherein said tube is made of elastomer.

4. A suction control apparatus according to claim 2, wherein said cut is at an angle of from 15 to 60 degrees to the axis of said tube.

5. A suction control apparatus according to claim 4, wherein said cut is at an angle of 30 degrees to the axis of said tube.

6. A suction control apparatus according to claim 2, wherein said switching means has a slider which is slidable along the outer surface of said tube and a control button which causes said slider to slide in response to a manual operation.

7. A suction control apparatus provided on an control part of an endoscope having a suction port at the distal end of an insert part thereof, comprising:
- a flexible tube communicating at the distal end thereof with said suction port and communicably connected at the proximal end thereof to a suction means;
- a cut made in the intermediate portion of said tube so as to extend obliquely from the proximal end side toward the distal end side of said tube; and
- switching means for contacting said tube at said cut for switching over the following two states from one to the other, that is, a stand-by state wherein said tube is diametrically pressed at said cut from the side of said tube and a suction state wherein said tube is restored to its free state, thereby enabling suction to take place from the distal end side to the proximal end side of said tube.

8. A suction control apparatus according to claim 7, said tube having an outer surface and an inner surface, wherein a flap is formed at the distal end side of said cut, said flap having a tip, whereby the outer surface of said tip is disposed at said inner surface of the proximal end side of said cut when said cut is closed.

9. A suction control apparatus provided on an control part of an endoscope having a suction port at the distal end of an insert part thereof, comprising:
- a flexible tube communicating at the distal end thereof with said suction port and communicably connected at the proximal end thereof to a suction means;
- a cut made in the intermediate portion of said tube so as to extend obliquely from the proximal end side toward the distal end side of said tube; and
- switching means for contacting said tube at said cut for switching over the following two states from one to the other, that is, a stand-by state wherein said tube is diametrically presses at said cut from the side of said tube where said cut is provided so as to close the cut area which leads to the distal end of said tube and a suction state wherein said tube is restored to its free state, thereby enabling suction to take place from the distal end side to the proximal end side of said tube.

10. A suction control apparatus according to claim 9, wherein said tube is made of elastomer.

11. A suction control apparatus according to claim 9, wherein said cut is at an angle of from 15 to 60 degrees to the axis of said tube.

12. A suction control apparatus according to claim 11, wherein said cut is at an angle of 30 degrees to the axis of said tube.

13. A suction control apparatus according to claim 9, wherein said switching means has a pressing plate which is slidable in the diametrical direction of said tube so that said pressing plate can press said tube from the side thereof where said cut is provided and thereby close said tube, and a control button which causes said pressing plate to slide in response to a manual operation.

14. A suction control apparatus provided on a control part of an endoscope having a suction port at the distal end of an insert part thereof, comprising:
- a flexible tube communicating at the distal end thereof with said suction port and communicably connected at the proximal end thereof to a suction means;
- a cut made in the intermediate portion of said tube so as to extend obliquely from the proximal end side toward the distal end side of said tube; and
- switching means for switching over the following two states from one to the other, that is, a stand-by state wherein said tube is bent diametrically pressed at said cut from the side of said tube where said cut is provided so as to close the cut area which leads to the distal end of said tube and a suction state wherein said tube is restored to its free state, thereby enabling suction to take place from the distal end side to the proximal end side of said tube, wherein said switching means has a pressing plate which is slidable in the diametrical direction of said tube so that said pressing plate can press said tube from the side thereof where said cut is provided and thereby close said tube, and a control button which causes said pressing plate to slide in response to a manual operation.

15. A suction control apparatus according to claim 14, wherein said pressing plate is provided with a bore for receiving said tube.

16. A suction control apparatus according to claim 15, wherein one side of said bore is open so that said tube can be inserted into and removed from said bore through the open portion.

17. A suction control apparatus provided on an control part of an endoscope having a suction port at the distal end of an insert part thereof, comprising:
- a flexible tube communicating at the distal end thereof with said suction port and communicably connected at the proximal end thereof to a suction means;
- a cut made in the intermediate portion of said tube so as to extend obliquely from the proximal end side toward the distal end side of said tube; and
- switching means for switching over the following two states from one to the other, that is, a state wherein said tube is bent with said cut facing outward and a state wherein said tube is straightened at and near said cut, wherein said switching means includes a slider which is slidable along the outer surface of said tube and a control button which causes said slides to slide in response to manual operation;

whereby, when said tube is bent, said cut is opened and ambient air is sucked into said tube through said cut, whereas, when said tube is straightened, said cut is closed and suction is performed through said suction port.

18. A suction control apparatus according to claim 17, wherein said slider has an annular configuration.

19. A suction control apparatus according to claim 17, wherein said slider has a C-shaped cross-sectional configuration so that said tube can be attached to and removed from said slider through the opening in the C-shaped configuration.

* * * * *

UNITED STATES PATENT AND TRADEMARK OFFICE
CERTIFICATE OF CORRECTION

PATENT NO. : 5,057,080
DATED : October 15, 1991
INVENTOR(S) : Nagashige TAKAHASHI It is certified that error appears in the above-indentified patent and that said Letters Patent is hereby corrected as shown below:

On the title page, section [57], line 13 of the abstract, change "to the," to ---to the other;---.
    On the title page, section [57], line 17 of the abstract, change "the ambient" to ---ambient---.
    At column 9, line 55 (claim 7, line 1), change "on an" to ---on a---.
    At column 10, line 11 (claim 9, line 1), change "on an" to ---on a---.
    At column 11, line 12 (claim 17, line 1), change "on an" to ---on a---.

Signed and Sealed this

Twenty-first Day of March, 1995

Attest:

BRUCE LEHMAN

*Attesting Officer*       *Commissioner of Patents and Trademarks*